US011114578B2

(12) United States Patent
Cao et al.

(10) Patent No.: US 11,114,578 B2
(45) Date of Patent: Sep. 7, 2021

(54) IMAGE SENSORS WITH SILVER-NANOPARTICLE ELECTRODES

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/130,721

(22) Filed: Dec. 22, 2020

(65) Prior Publication Data

US 2021/0111217 A1 Apr. 15, 2021

Related U.S. Application Data

(63) Continuation of application No. PCT/CN2018/095523, filed on Jul. 12, 2018.

(51) Int. Cl.
*H01L 31/107* (2006.01)
*G01N 23/046* (2018.01)
(Continued)

(52) U.S. Cl.
CPC ....... *H01L 31/1075* (2013.01); *G01N 23/046* (2013.01); *G01N 23/083* (2013.01);
(Continued)

(58) Field of Classification Search
CPC ............... H01L 29/66113; H01L 31/00; H01L 31/02019; H01L 31/02027; H01L 31/107;
(Continued)

(56) References Cited

U.S. PATENT DOCUMENTS 4,949,144 A * 8/1990 Kuroda ............. H01L 21/26546
257/185
5,155,351 A * 10/1992 Yamanobe ........ H01L 27/14623
257/435
(Continued)

FOREIGN PATENT DOCUMENTS

EP 2184788 A1 5/2010
WO 2017219224 A1 12/2017

*Primary Examiner* — Eduardo A Rodela
(74) *Attorney, Agent, or Firm* — IPro, PLLC; Qian Gu

(57) ABSTRACT

Disclosed herein is an apparatus comprising: an array of avalanche photodiodes (APDs) or an absorption region comprising a semiconductor single crystal such as a CdZnTe single crystal or a CdTe single crystal. The apparatus may be configured to absorb radiation particles incident on an absorption region of the APDs or the semiconductor single crystal and to generate charge carriers. The apparatus may comprise an electrode comprising silver nanoparticles and being electrically connected to the absorption region of the APDs or the semiconductor single crystal. For the APDs, each of the APDs may comprise an amplification region, which may comprise a junction with an electric field in the junction. The electric field may be at a value sufficient to cause an avalanche of charge carriers entering the amplification region, but not sufficient to make the avalanche self-sustaining. The junctions of the APDs may be discrete.

33 Claims, 15 Drawing Sheets

(51) Int. Cl.
*G01N 23/083* (2018.01)
*H01L 27/146* (2006.01)
*H01L 31/0224* (2006.01)
*H01L 31/028* (2006.01)
*H01L 31/0296* (2006.01)
*H01L 31/0304* (2006.01)
*H01L 31/02* (2006.01)
*H01L 29/66* (2006.01)
*A61B 6/03* (2006.01)

(52) U.S. Cl.
CPC .. *H01L 27/14659* (2013.01); *H01L 29/66113* (2013.01); *H01L 31/028* (2013.01); *H01L 31/02027* (2013.01); *H01L 31/0296* (2013.01); *H01L 31/02966* (2013.01); *H01L 31/022408* (2013.01); *H01L 31/0304* (2013.01); *H01L 31/107* (2013.01); *A61B 6/035* (2013.01)

(58) Field of Classification Search
CPC ........... H01L 31/1075; H01L 27/14659; H01L 31/022408; H01L 31/028; H01L 31/0304; H01L 31/0296; H01L 31/02966; G01N 23/083; G01N 23/046; A61B 6/035
See application file for complete search history.

(56) References Cited

U.S. PATENT DOCUMENTS

| | | | | |
|---|---|---|---|---|
| 8,829,452 | B1* | 9/2014 | Brown | H01L 31/1075 250/370.07 |
| 9,847,437 | B1* | 12/2017 | You | H01L 31/022425 |
| 2002/0024058 | A1* | 2/2002 | Marshall | H04N 5/3745 257/170 |
| 2002/0185700 | A1* | 12/2002 | Coffa | H01L 31/107 257/431 |
| 2008/0067620 | A1 | 3/2008 | Rothman | |
| 2011/0018086 | A1* | 1/2011 | Linga | H01L 31/1075 257/438 |
| 2015/0330836 | A1 | 11/2015 | Kautzsch | |
| 2018/0019268 | A1* | 1/2018 | Zhang | H01L 31/107 |
| 2018/0374890 | A1* | 12/2018 | Cao | H01L 27/14609 |
| 2019/0267509 | A1* | 8/2019 | Takeuchi | H01L 31/167 |
| 2020/0168659 | A1* | 5/2020 | Cumming | H01L 31/1035 |
| 2020/0249366 | A1* | 8/2020 | Cao | G01T 1/248 |
| 2020/0249367 | A1* | 8/2020 | Cao | A61B 6/50 |
| 2020/0256992 | A1* | 8/2020 | Cao | G01S 7/4816 |
| 2020/0335546 | A1* | 10/2020 | Miura | H01L 27/1443 |

* cited by examiner

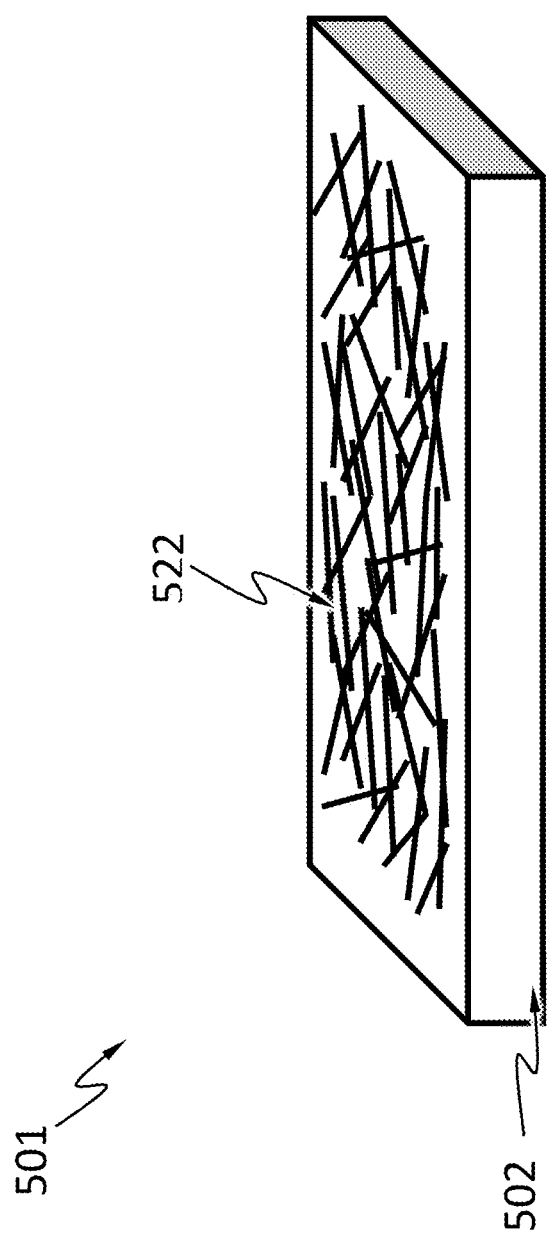

IMAGE SENSORS WITH SILVER-NANOPARTICLE ELECTRODES

TECHNICAL FIELD

The disclosure herein relates to image sensors, particularly relates to image sensors with silver-nanoparticle electrodes.

BACKGROUND

An image sensor or imaging sensor is a sensor that can detect a spatial intensity distribution of a radiation. The radiation may be an electromagnetic radiation such as infrared light, visible light, ultraviolet light, X-ray or γ-ray. The radiation may be of other types such as α-rays and β-rays. The radiation may be one that has interacted with a subject. For example, the radiation measured by an image sensor may be a radiation that has penetrated or reflected from the subject.

An image sensor usually represents the detected image by electrical signals. Image sensors based on semiconductor devices may be classified into several types, including semiconductor charge-coupled devices (CCD), complementary metal-oxide-semiconductor (CMOS), N-type metal-oxide-semiconductor (NMOS). A CMOS image sensor is a type of active pixel sensor made using the CMOS semiconductor process. Light incident on a pixel in the CMOS image sensor is converted into an electric voltage. The electric voltage is digitized into a discrete value that represents the intensity of the light incident on that pixel. An active-pixel sensor (APS) is an image sensor that includes pixels with a photodetector and an active amplifier. A CCD image sensor includes a capacitor in a pixel. When light incidents on the pixel, the light generates electrical charges and the charges are stored on the capacitor. The stored charges are converted to an electric voltage and the electrical voltage is digitized into a discrete value that represents the intensity of the light incident on that pixel.

SUMMARY

Disclosed herein is an apparatus comprising: an array of avalanche photodiodes (APDs), each of the APDs comprising an absorption region, an electrode and a first amplification region; wherein the absorption region is configured to generate charge carriers from a photon absorbed by the absorption region; wherein the electrode comprises silver nanoparticles and is electrically connected to the absorption region; wherein the first amplification region comprises a junction with an electric field in the junction; wherein the electric field is at a value sufficient to cause an avalanche of charge carriers entering the first amplification region, but not sufficient to make the avalanche self-sustaining; wherein the junctions of the APDs are discrete.

According to an embodiment, each of the APDs further comprises a second amplification region between the absorption region and the electrode, wherein the first amplification region and the second amplification region are on opposite sides of the absorption region.

According to an embodiment, the silver nanoparticles comprise silver nanowires.

According to an embodiment, a number density of the silver nanoparticles is above an electrical percolation threshold of the silver nanoparticles.

According to an embodiment, the electrode further comprises a conductive pad in electrical contact with a portion of the silver nanoparticles.

According to an embodiment, the electrode is a common electrode shared by the absorption regions of the array of APDs.

According to an embodiment, the electrode further comprises a coating layer on the silver nanoparticles.

According to an embodiment, the photon is a soft X-ray photon.

According to an embodiment, the absorption region has a thickness of 10 microns or above.

According to an embodiment, the absorption region comprises silicon.

According to an embodiment, an electric field in the absorption region is not high enough to cause avalanche effect in the absorption region.

According to an embodiment, the absorption region is an intrinsic semiconductor or a semiconductor with a doping level less than $10^{12}$ dopants/cm$^3$.

According to an embodiment, the absorption regions of at least some of the APDs are joined together.

According to an embodiment, the first amplification regions of the APDs are discrete.

According to an embodiment, the junction is a p-n junction or a heterojunction.

According to an embodiment, the junction comprises a first layer and a second layer, wherein the first layer is a doped semiconductor and the second layer is a heavily doped semiconductor.

According to an embodiment, the first layer has a doping level of $10^{13}$ to $10^{17}$ dopants/cm$^3$.

According to an embodiment, the first layers of least some of the APDs are joined together.

According to an embodiment, the junction is separated from a junction of a neighbor junction by a material of the absorption region, a material of the first or second layer, an insulator material, or a guard ring of a doped semiconductor.

According to an embodiment, the guard ring is a doped semiconductor of a same doping type as the second layer and the guard ring is not heavily doped.

According to an embodiment, the junction further comprises a third layer sandwiched between the first and second layers; wherein the third layer comprises an intrinsic semiconductor.

According to an embodiment, the third layers of at least some of the APDs are joined together.

Disclosed herein is an apparatus comprising: a substrate; a semiconductor single crystal in a recess in the substrate; an electrode on the semiconductor single crystal; wherein the apparatus is configured to absorb radiation particles incident on the semiconductor single crystal and to generate charge carriers; wherein the electrode comprises silver nanoparticles and is electrically connected to the semiconductor single crystal.

According to an embodiment, the silver nanoparticles are silver nanowires.

According to an embodiment, a number density of the silver nanoparticles is above an electrical percolation threshold of the silver nanoparticles.

According to an embodiment, the electrode further comprises a conductive pad in electrical contact with a portion of the silver nanoparticles.

According to an embodiment, the electrode further comprises a coating layer on the silver nanoparticles.

According to an embodiment, the semiconductor single crystal is a CdZnTe single crystal or a CdTe single crystal.

According to an embodiment, the substrate comprises silicon, germanium, GaAs or a combination thereof.

According to an embodiment, a surface of the semiconductor single crystal and a surface of the substrate are coextensive.

According to an embodiment, the apparatus further comprises another electrode in electrical contact with the semiconductor single crystal; an electronics layer bonded to the substrate, the electronics layer comprising an electronic system configured to process an electrical signal generated from the charge carriers collected by the other electrode.

According to an embodiment, the electronic system comprises a voltage comparator configured to compare a voltage of the electrode to a first threshold; a counter configured to register a number of radiation particles absorbed by the substrate; a controller; a voltmeter; wherein the controller is configured to start a time delay from a time at which the voltage comparator determines that an absolute value of the voltage equals or exceeds an absolute value of the first threshold; wherein the controller is configured to cause the voltmeter to measure the voltage upon expiration of the time delay; wherein the controller is configured to determine a number of radiation particles by dividing the voltage measured by the voltmeter by a voltage that a single radiation particle would have caused on the other electrode; wherein the controller is configured to cause the number registered by the counter to increase by the number of radiation particles.

Disclosed herein is a system comprising any of the above apparatuses and an X-ray source, wherein the system is configured such that the apparatus forms an image of an object using X-ray from the X-ray source that penetrated the object.

DETAILED DESCRIPTION

An avalanche photodiode (APD) is a photodiode that uses the avalanche effect to generate an electric current upon exposure to light. The avalanche effect is a process where free charge carriers in a material are subjected to strong acceleration by an electric field and subsequently collide with other atoms of the material, thereby ionizing them (impact ionization) and releasing additional charge carriers which accelerate and collide with further atoms, releasing more charge carriers—a chain reaction. Impact ionization is a process in a material by which one energetic charge carrier can lose energy by the creation of other charge carriers. For example, in semiconductors, an electron (or hole) with enough kinetic energy can knock a bound electron out of its bound state (in the valence band) and promote it to a state in the conduction band, creating an electron-hole pair.

An APD may work in the Geiger mode or the linear mode. When the APD works in the Geiger mode, it may be called a single-photon avalanche diode (SPAD) (also known as a Geiger-mode APD or G-APD). A SPAD is an APD working under a reverse bias above the breakdown voltage. Here the word "above" means that absolute value of the reverse bias is greater than the absolute value of the breakdown voltage. A SPAD may be used to detect low intensity light (e.g., down to a single photon) and to signal the arrival times of the photons with a jitter of a few tens of picoseconds. A SPAD may be in a form of a p-n junction under a reverse bias (i.e., the p-type region of the p-n junction is biased at a lower electric potential than the n-type region) above the breakdown voltage of the p-n junction. The breakdown voltage of a p-n junction is a reverse bias, above which exponential increase in the electric current in the p-n junction occurs. An APD working at a reverse bias below the breakdown voltage is operating in the linear mode because the electric current in the APD is proportional to the intensity of the light incident on the APD.

Figure 1:
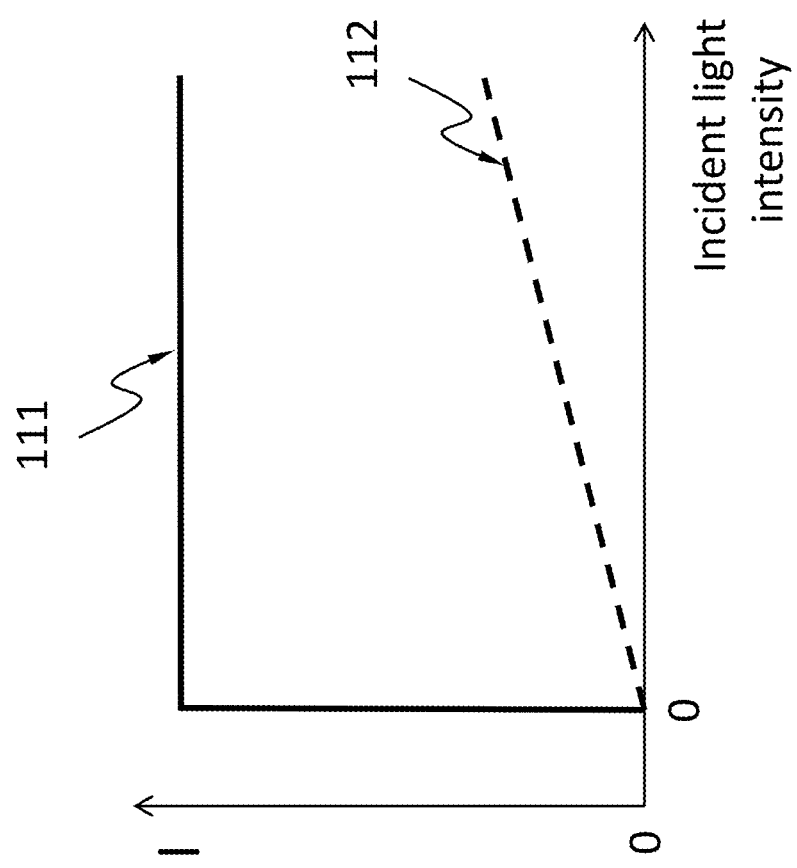
FIG. 1 schematically shows the electric current in an APD as a function of the intensity of light incident on the APD when the APD is in the linear mode, and a function of the intensity of light incident on the APD when the APD is in the Geiger mode.

FIG. 1 schematically shows the electric current in an APD as a function 112 of the intensity of light incident on the APD when the APD is in the linear mode, and a function 111 of the intensity of light incident on the APD when the APD is in the Geiger mode (i.e., when the APD is a SPAD). In the Geiger mode, the current shows a very sharp increase with the intensity of the light and then saturation. In the linear mode, the current is essentially proportional to the intensity of the light.

Figure 2C:
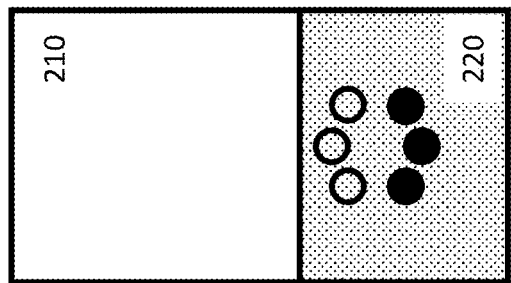
FIG. 2A, FIG. 2B and FIG. 2C schematically show the operation of an APD, according to an embodiment.
Figure 2B:
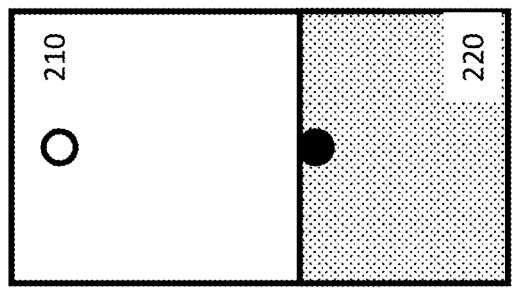
Figure 2A:
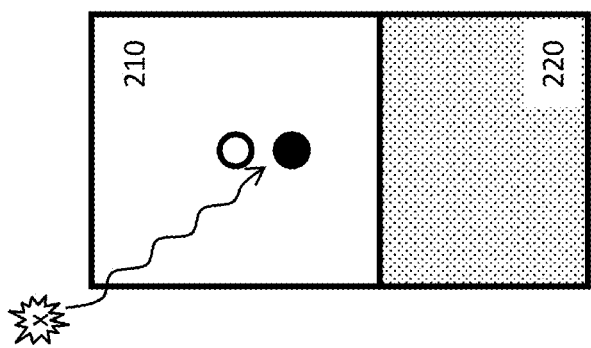

FIG. 2A, FIG. 2B and FIG. 2C schematically show the operation of an APD, according to an embodiment. FIG. 2A shows that when a photon (e.g., an X-ray photon) is absorbed by an absorption region 210, multiple (100 to 10000 for an X-ray photon) electron-hole pairs maybe generated. The absorption region 210 has a sufficient thickness and thus a sufficient absorptance (e.g., >80% or >90%) for the incident photon. For soft X-ray photons, the absorption region 210 may be a silicon layer with a thickness of 10 microns or above. The electric field in the absorption region 210 is not high enough to cause avalanche effect in the absorption region 210. FIG. 2B shows that the electrons and hole drift in opposite directions in the absorption region 210. FIG. 2C shows that avalanche effect occurs in an amplification region 220 when the electrons (or the holes) enter that amplification region 220, thereby generating more electrons and holes. The electric field in the amplification region 220 is high enough to cause an avalanche of charge carriers entering the amplification region 220 but not too high to make the avalanche effect self-sustaining. A self-sustaining avalanche is an avalanche that persists after the external triggers disappear, such as photons incident on the APD or charge carriers drifted into the APD. The electric field in the amplification region 220 may be a result of a doping profile in the amplification region 220. For example, the amplification region 220 may include a p-n junction or a heterojunction that has an electric field in its depletion zone. The threshold electric field for the avalanche effect (i.e., the electric field above which the avalanche effect occurs and below which the avalanche effect does not occur) is a property of the material of the amplification region 220. The amplification region 220 may be on one or two opposite sides of the absorption region 210.

Figure 3A:
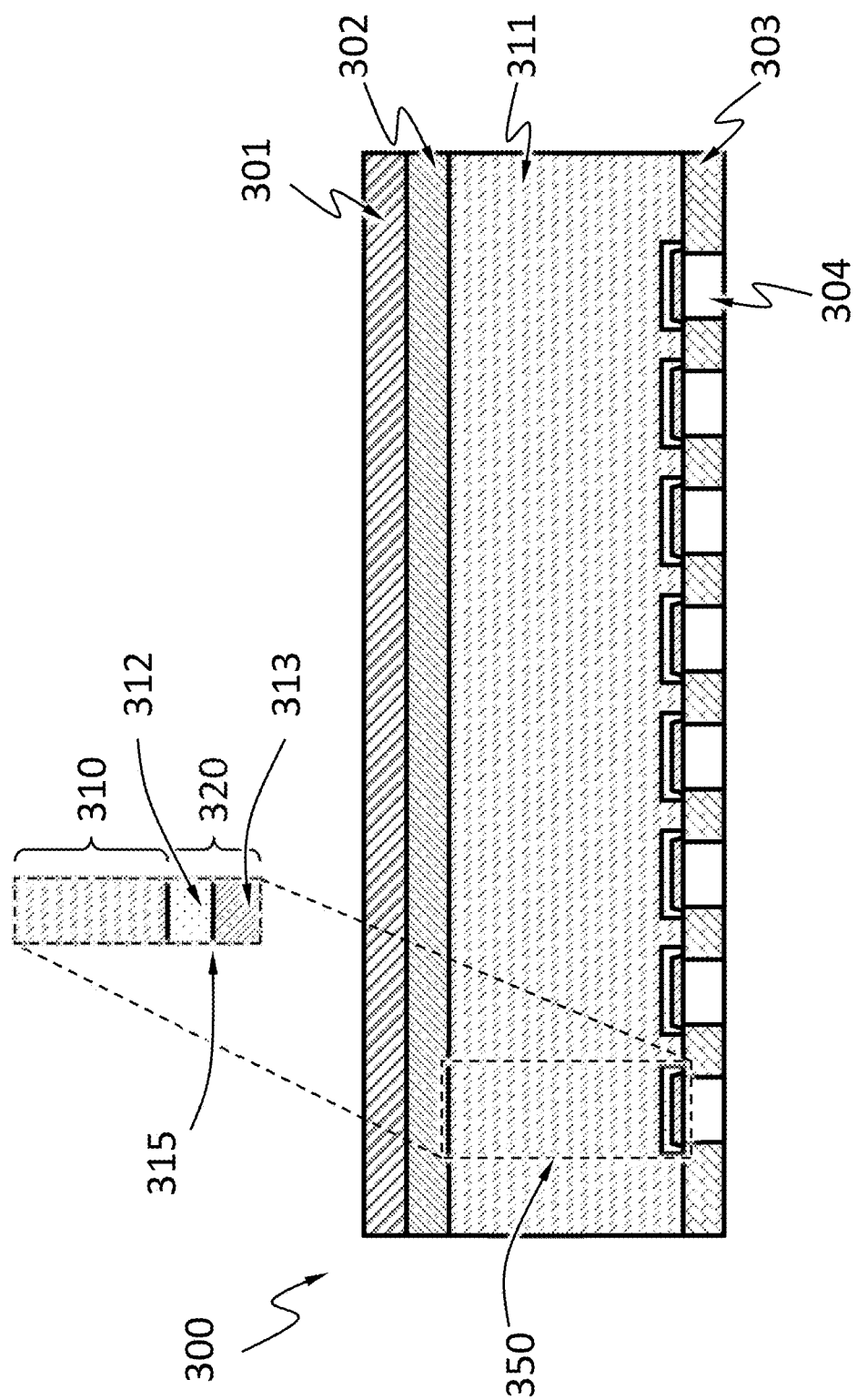
FIG. 3A schematically shows a cross section of an image sensor based on an array of APDs, according to an embodiment.

FIG. 3A schematically shows a cross section of an image sensor 300 based on an array of APDs 350. Each of the APDs 350 may have an absorption region 310 and a first amplification region 320 as the example shown in FIG. 2A, FIG. 2B and FIG. 2C, as well as an electrode 301. At least some, or all, of the APDs 350 in the image sensor 300 may have their absorption regions 310 joined together. Namely, the image sensor 300 may have joined absorption regions 310 in a form of an absorption layer 311 that is shared among at least some or all of the APDs 350. The first amplification regions 320 of the APDs 350 are discrete regions. Namely the first amplification regions 320 of the APDs 350 are not joined together. The electrode 301 is electrically connected to the absorption region 310. The electrode 301 of at least some or all of the APDs 350 may be joined together. In an embodiment, the electrode 301 may be a common electrode shared by the absorption regions 310 of the APDs 350. The image sensor 300 may further include a heavily doped layer 302 disposed on the absorption regions 310 opposite to the first amplification region 320, and the electrode 301 may be on the heavily doped layer 302. The electrode 301 of at least some or all of the APDs 350 may be joined together. The heavily doped layer 302 of at least some or all of the APDs 350 may be joined together. In an embodiment, each of the APDs 350 further comprises a second amplification region between the absorption region 310 and the electrode 301.

The image sensor 300 may further include electrodes 304 respectively in electrical contact with the layer 313 of the APDs 350. The electrodes 304 are configured to collect electric current flowing through the APDs 350.

The image sensor 300 may further include a passivation material 303 configured to passivate surfaces of the absorption regions 310 and the layer 313 of the APDs 350 to reduce recombination at these surfaces.

In an embodiment, the absorption layer 311 may be in form of a semiconductor wafer such as a silicon wafer. The absorption regions 310 may be an intrinsic semiconductor or very lightly doped semiconductor (e.g., $<10^{12}$ dopants/cm$^3$, $<10^{11}$ dopants/cm$^3$, $<10^{10}$ dopants/cm$^3$, $<10^9$ dopants/cm$^3$), with a sufficient thickness and thus a sufficient absorptance (e.g., >80% or >90%) for incident photons of interest (e.g., X-ray photons). The first amplification regions 320 may have a junction 315 formed by at least two layers 312 and 313. The junction 315 may be a heterojunction of a p-n junction. In an embodiment, the layer 312 is a p-type semiconductor (e.g., silicon) and the layer 313 is a heavily doped n-type layer (e.g., silicon). The phrase "heavily doped" is not a term of degree. A heavily doped semiconductor has its electrical conductivity comparable to metals and exhibits essentially linear positive thermal coefficient. In a heavily doped semiconductor, the dopant energy levels are merged into an energy band. A heavily doped semiconductor is also called degenerate semiconductor. The layer 312 may have a doping level of $10^{13}$ to $10^{17}$ dopants/cm$^3$. The layer 313 may have a doping level of $10^{18}$ dopants/cm$^3$ or above. The layers 312 and 313 may be formed by epitaxy growth, dopant implantation or dopant diffusion. The band structures and doping levels of the layers 312 and 313 can be selected such that the depletion zone electric field of the junction 315 is greater than the threshold electric field for the avalanche effect for electrons (or for holes) in the materials of the layers 312 and 313, but is not too high to cause self-sustaining avalanche. Namely, the depletion zone electric field of the junction 315 should cause avalanche when there are incident photons in the absorption region 310 but the avalanche should cease without further incident photons in the absorption region 310.

The junctions 315 of the APDs 350 should be discrete, i.e., the junction 315 of one of the APDs 350 should not be joined with the junction 315 of another one of the APDs 350. Charge carriers amplified at one of the junctions 315 of the APDs 350 should not be shared with another of the junctions 315. The junction 315 of one of the APDs 350 may be separated from the junction 315 of the neighboring APDs 350 by the material of the absorption region wrapping around the junction, by the material of the layer 312 or 313 wrapping around the junction, by an insulator material wrapping around the junction, or by a guard ring of a doped semiconductor. As shown in FIG. 3A, the layer 312 of each of the APDs 350 may be discrete, i.e., not joined with the layer 312 of another one of the APDs 350; the layer 313 of each of the APDs 350 may be discrete, i.e., not joined with the layer 313 of another one of the APDs 350.

Figure 3B:
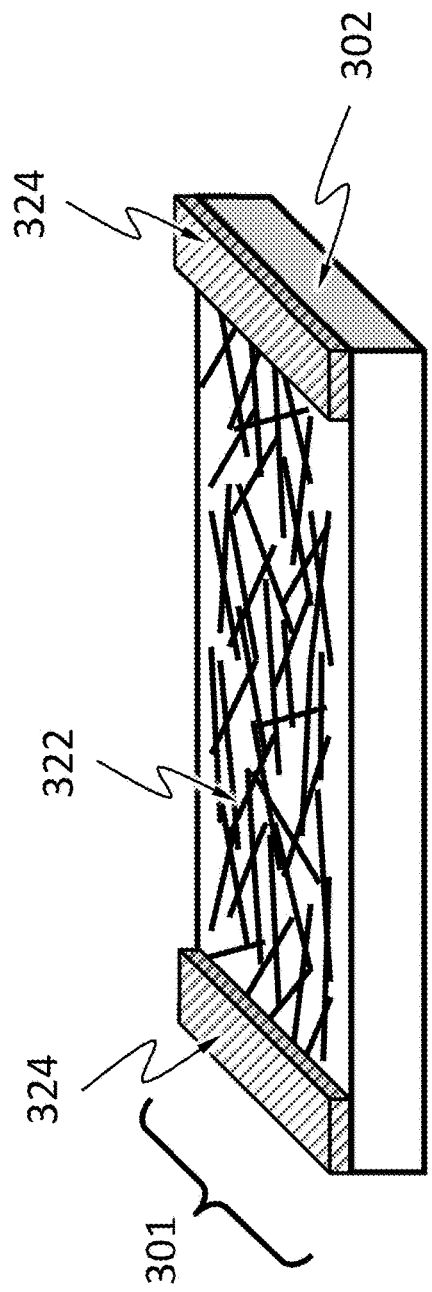
FIG. 3B and FIG. 3C schematically shows a perspective view of the electrode comprising silver nanoparticles, according to an embodiment.
Figure 3C:
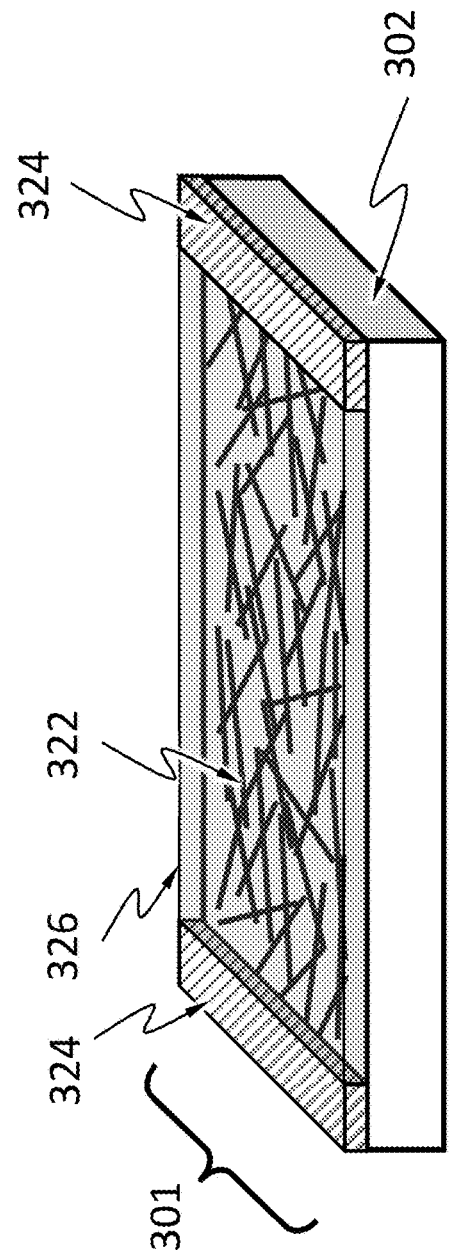

The electrode 301 may comprise silver nanoparticles 322 as shown in FIG. 3B and FIG. 3C. The silver nanoparticles 322 may have a number density above an electrical percolation threshold of the silver nanoparticles 322 in the electrode 301. The electrical percolation threshold is a critical number density of the silver nanoparticles 322, above which the silver nanoparticles 322 of the electrode 301 may contact one another and form an electrically conductive path allowing charge carriers to flow through. In an embodiment, the silver nanoparticles 322 may comprise silver nanowires, and the silver nanowires may form a conductive network as shown in FIG. 3B and FIG. 3C. The silver nanoparticles 322 may form electrical contact (e.g., Ohmic contact) with the absorption region 310 or the heavily doped layer 302. The electrode 301 may further comprise a conductive pad 324 in electrical contact with a portion of the silver nanoparticles 322. The silver nanoparticles 322 may have various geometries, sizes, shapes or aspect ratios (e.g., ratio of the sizes of the silver nanoparticles in different dimensions). For instance, the silver nanowires in FIG. 3B and FIG. 3C may have lengths of nanometers or micrometers, and diameters of nanometers to hundreds of nanometers. The silver nanoparticles 322 may also be spheres or other anisotropic structures besides nanowires, or may be a hybrid of various shapes.

The electrode 301 may be a hybrid electrode, which further comprises a coating layer 326 on the silver nanoparticles 322, as shown in FIG. 3C. The coating layer 326 may comprise insulating materials such as heat resistant polymers, or conductive materials such as conducting polymers, indium tin oxide (ITO), graphene, silver, etc. The coating layer 326 may improve mechanical strength of the electrode 301 and help protect the silver nanoparticles 322. The conductivity of the electrode 301 may be determined by intrinsic conductivity of the silver nanoparticles 322, the number density of the silver nanoparticles 322, geometry of the silver nanoparticles 322, and the coating material, etc. In an embodiment, the conductivity of the electrode 301 may be comparable to that of bulk silver. The electrode 301 may be transparent to light with wavelength in a variety of regions, such as X-ray region, visible region and infrared region. For instance, the transmittance of the electrode 301 in visible light region and infrared region may reach to 70%, 80%, 90%, and above.

When a photon incidents on the image sensor 300, it may be absorbed by the absorption region 310 of one of the APDs 350, and charge carriers may be generated in the absorption region 310 as a result. One type (electrons or holes) of the charge carriers may drift toward the first amplification region 320 of that one APD. When the one type of charge carriers enters the first amplification region 320, the avalanche effect occurs and causes amplification of the charge carriers. The amplified charge carriers can be collected through the electrode 304 of that one APD 350, as an electric current. The other type of charge carriers (holes or electrons) generated in the absorption region 310, or amplified in the second amplification region if one exists, may flow to the silver nanoparticles 322 and then be collected through the conductive pad 324. When that one APD 350 is in the linear mode, the electric current is proportional to the number of incident photons in the absorption region 310 per unit time (i.e., proportional to the light intensity at that one APD). The electric currents at the APDs 350 may be compiled to represent a spatial intensity distribution of light, i.e., an image. The amplified charge carriers may alternatively be collected through the electrode 304 of that one APD 350, and the number of photons may be determined from the charge carriers (e.g., by using the temporal characteristics of the electric current).

Figure 3D:
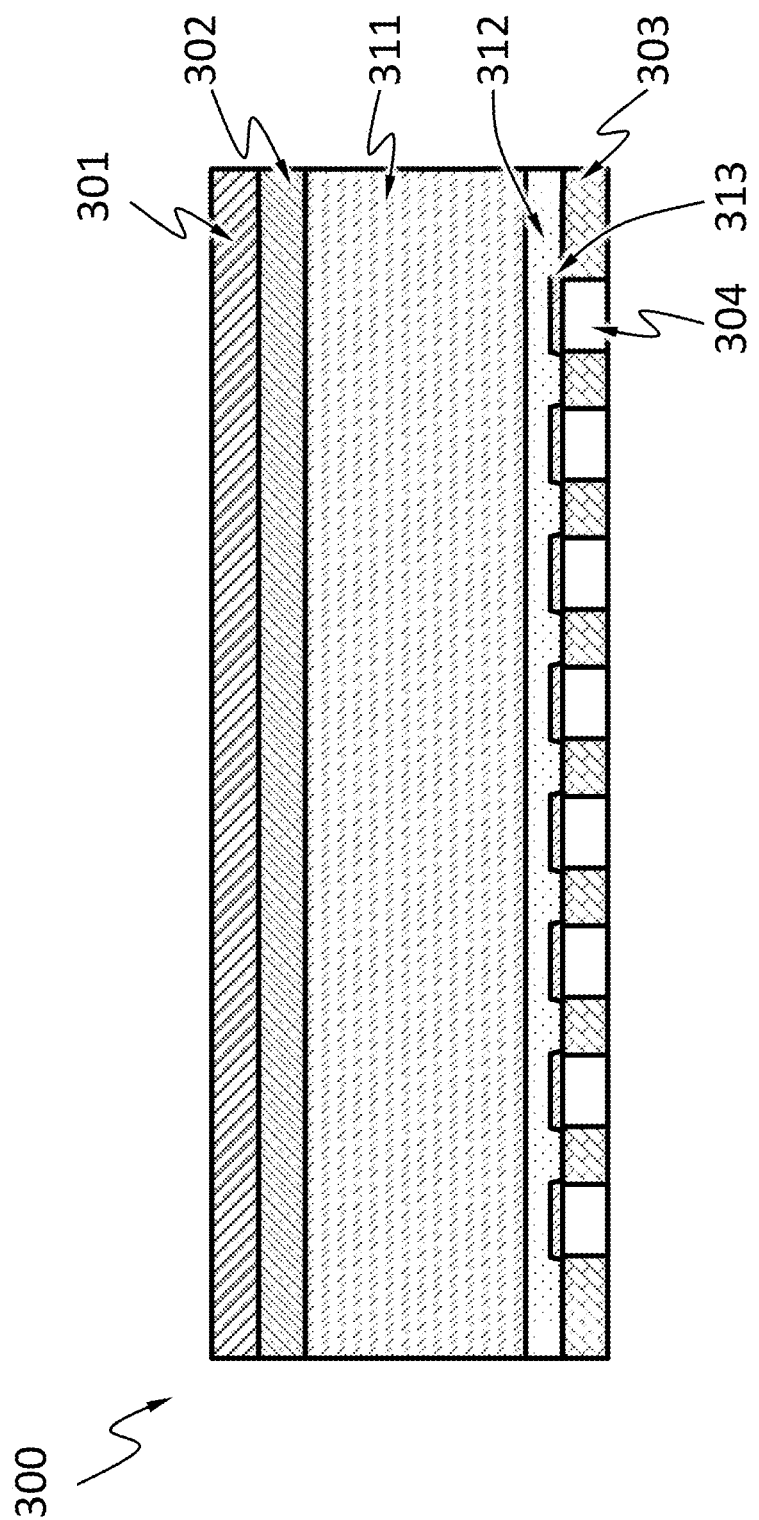
FIG. 3D shows a variant of the image sensor of FIG. 3A.
Figure 3E:
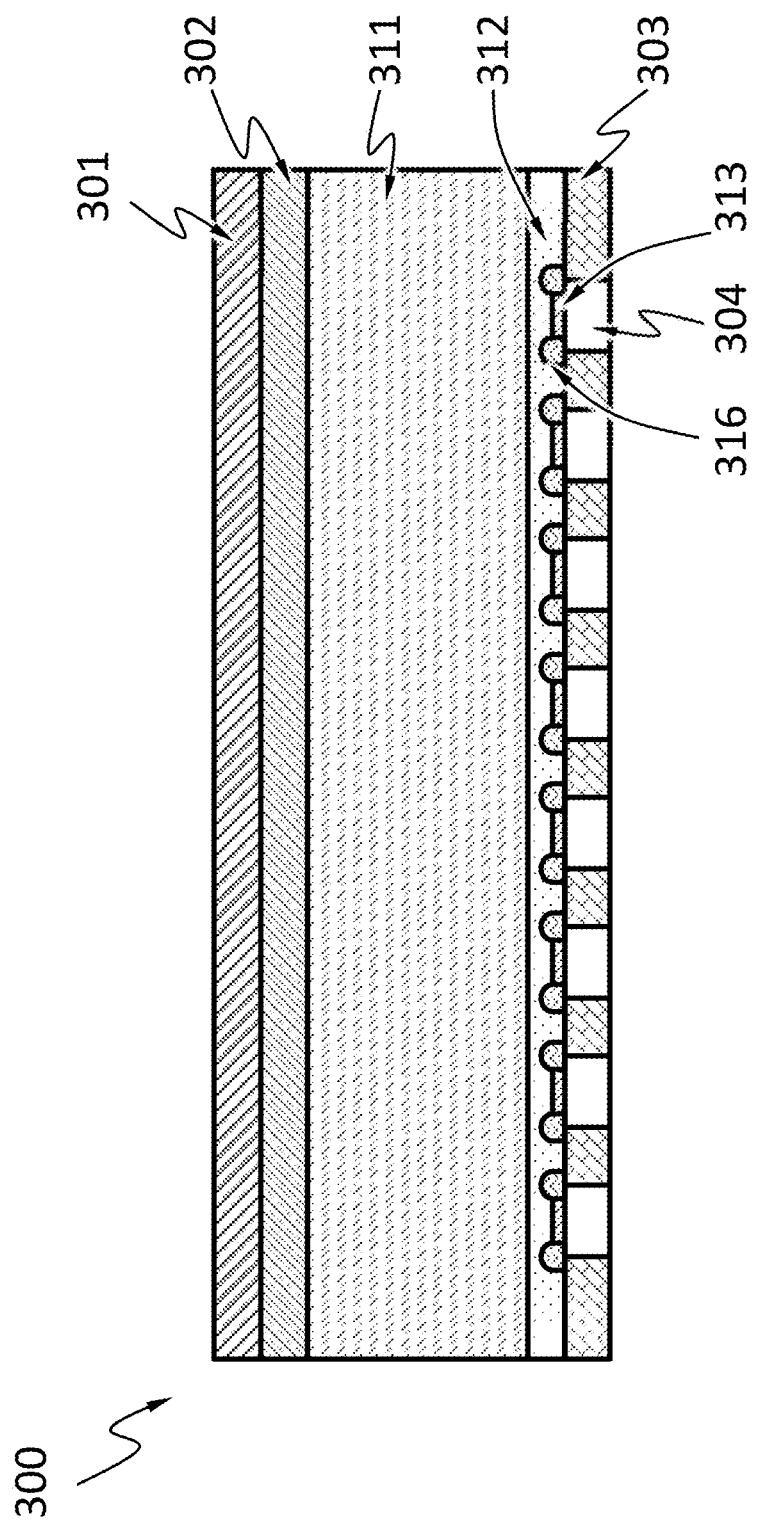
FIG. 3E shows a variant of the image sensor of FIG. 3A.
Figure 3F:
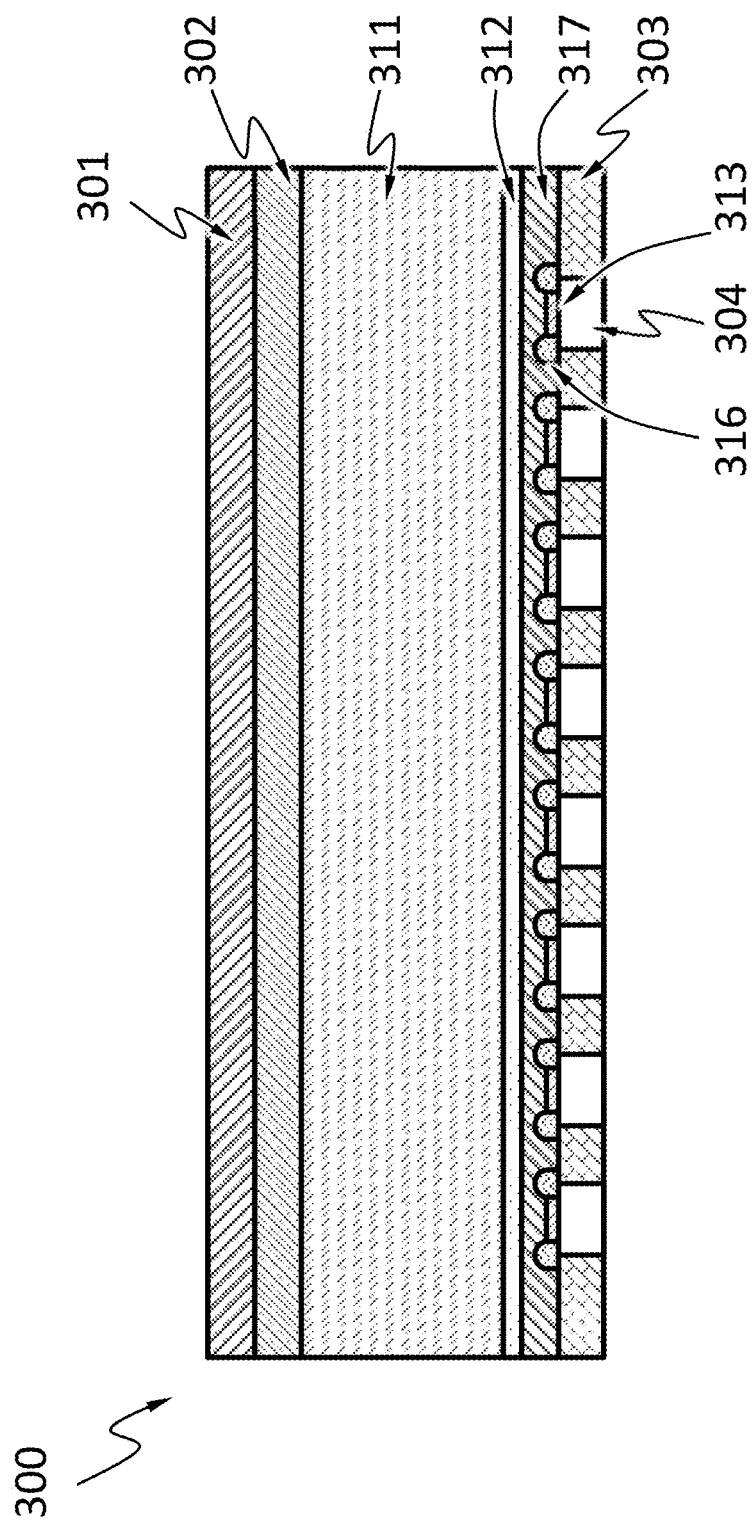
FIG. 3F shows a variant of the image sensor of FIG. 3A.

FIG. 3D shows a variant of the image sensor 300, where the layers 312 of some or all of the APDs 350 are joined together. FIG. 3E shows a variant of the image sensor 300, where the junction 315 is surrounded by a guard ring 316. The guard ring 316 may be an insulator material or a doped semiconductor. For example, when the layer 313 is heavily doped n-type semiconductor, the guard ring 316 may be n-type semiconductor of the same material as the layer 313 but not heavily doped. The guard ring 316 may be present in the image sensor 300 shown in FIG. 3A or FIG. 3D. FIG. 3F shows a variant of the image sensor 300, where the junction 315 has an intrinsic semiconductor layer 317 sandwiched between the layer 312 and 313. The intrinsic semiconductor layer 317 in each of the APDs 350 may be discrete, i.e., not joined with other intrinsic semiconductor layer 317 of another APD 350. The intrinsic semiconductor layers 317 of some or all of the APDs 350 may be joined together.

Figure 4A:
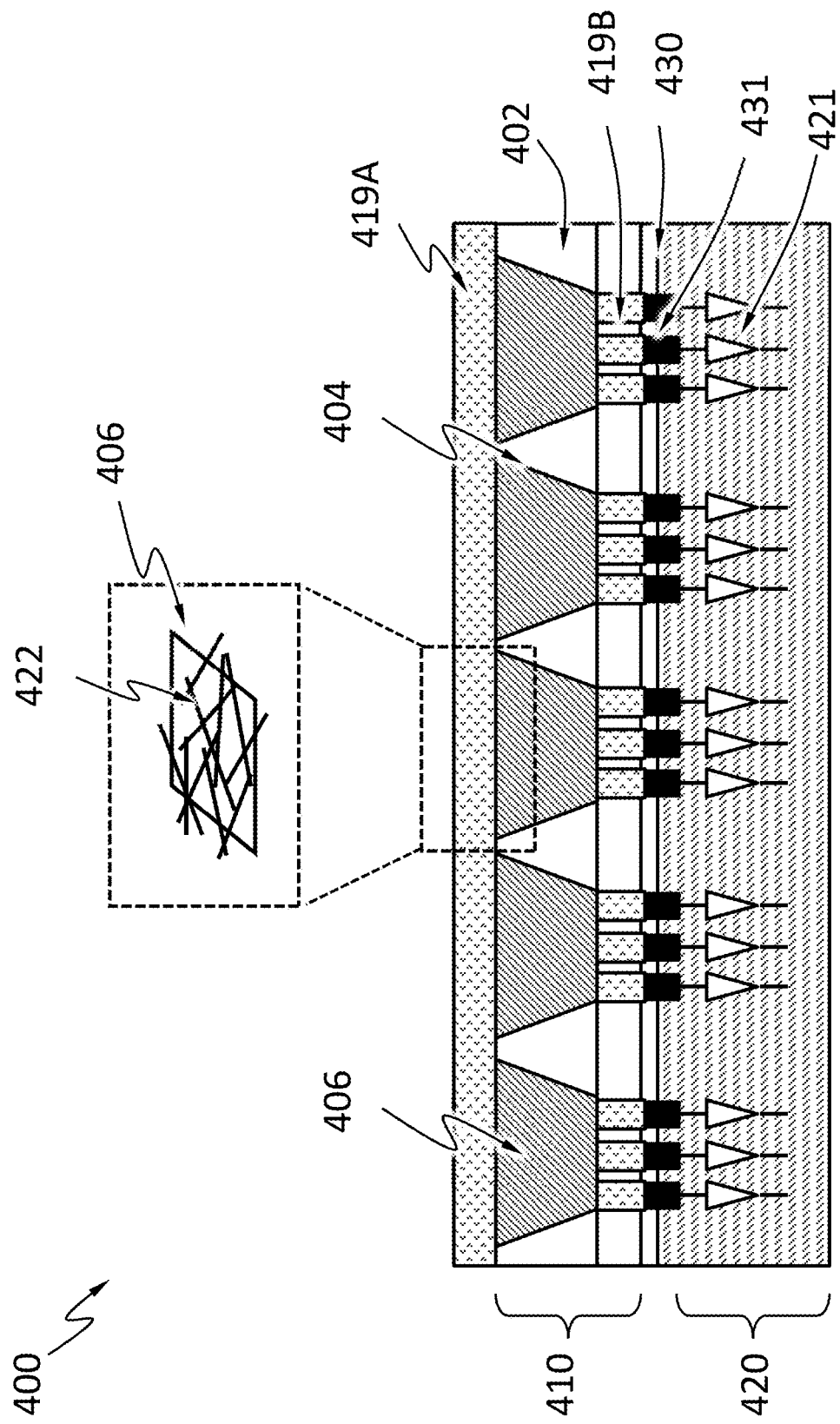
FIG. 4A schematically shows a detailed cross-sectional view of an image sensor, according to an embodiment.

FIG. 4A schematically shows a detailed cross-sectional view of an image sensor 400, according to an embodiment. The image sensor 400 may include a radiation absorption layer 410 configured to absorb an incident radiation and generate electrical signals from incident radiation, and an electronics layer 420 (e.g., an ASIC) for processing or analyzing the electrical signals generates in the radiation absorption layer 410.

The radiation absorption layer 410 may comprise a substrate 402, one or more recesses 404 in the substrate 402, each of which having a semiconductor single crystal 406 in it, and an electrode 419A on the one or more semiconductor single crystals 406. In an embodiment, at least some of the recesses 404 each have one and only one semiconductor single crystal 406, i.e., they each contain no other semiconductor material except the one semiconductor single crystal 406. The substrate 402 may comprise silicon, germanium, GaAs or a combination thereof. Each of the semiconductor single crystals 406 may be a cadmium zinc telluride (CdZnTe) single crystal, a cadmium telluride (CdTe) single crystal, or any other suitable single crystals that can be used to absorb radiation particles incident thereon and generate charge carriers. The electrode 419A may be an embodiment of the electrode 301 as shown in FIG. 3B and FIG. 3C. The silver nanoparticles 422 of the electrode 419A may be in electrical contact with the one or more single crystals 406. The radiation absorption layer 410 may further comprise another electrode 419B on a surface (e.g., an exposed surface, namely a surface not in direct physical contact with the substrate 402) of the semiconductor single crystals 406, and the electrode 419B may comprise discrete regions. Each of the semiconductor single crystals 406 may also be in contact with one or more discrete regions of the electrode 419B. The surface of the substrate 402 may be coextensive with the surface of each of the semiconductor single crystals 406. In an embodiment, the surface of each of the semiconductor single crystals 406 may accommodate tens or hundreds of the discrete regions of the electrode 419B. The electrode 419B may comprise a conducting material such as a metal (e.g., gold, copper, aluminum, platinum, etc.), or any other suitable conducting materials (e.g., a doped semiconductor). The electrodes 419A and 419B may be configured to collect the charge carriers (e.g., electrons and holes) generated in the semiconductor single crystal 406.

When the radiation hits the radiation absorption layer 410, the semiconductor single crystals 406 may absorb the radiation particles incident thereon and generate one or more charge carriers by a number of mechanisms. A particle of the radiation may generate 10 to 100000 charge carriers. The charge carriers may drift to the electrodes 419A and 419B under an electric field. The field may be an external electric field. In an embodiment, one type of charge carriers may drift in directions such that the charge carriers generated by a single particle of the radiation are not substantially shared by two different discrete portions of the electrode 419B ("not substantially shared" here means less than 2%, less than 0.5%, less than 0.1%, or less than 0.01% of these charge carriers flow to a different one of the discrete portions than the rest of the charge carriers). The one type of charge carriers generated by a radiation particle incident around the footprint of one of these discrete portions of the electrode 419B are not substantially shared with another of these discrete portions of the electrode 419B. An area around a discrete portion of the electrode 419B may be considered as a pixel associated with the discrete portion of the electrode 419B, where substantially all (more than 98%, more than 99.5%, more than 99.9% or more than 99.99% of) the one type of charge carriers generated by a particle of the radiation incident therein flow to the discrete portion of the electrode 419B. Namely, less than 2%, less than 0.5%, less than 0.1%, or less than 0.01% of these charge carriers flow beyond the pixel associated with the one discrete portion of the electrode 419B. The other type of charge carriers generated in the semiconductor single crystals 406 may flow to the silver nanoparticles 422 and then be collected through one or more conductive pads of the electrode 419A as in the examples shown in FIG. 3B and FIG. 3C.

The electronics layer 420 may include an electronic system 421 configured to process electrical signals on the electrode 419B generated from the charge carriers collected. The electronic system 421 may include an analog circuitry such as a filter network, amplifiers, integrators, and comparators, or a digital circuitry such as a microprocessor, and memory. The electronic system 421 may include one or more ADCs. The electronic system 421 may include components shared by the pixels or components dedicated to a single pixel. For example, the electronic system 421 may include an amplifier dedicated to each pixel and a microprocessor shared among all the pixels. The electronic system 421 may be electrically connected to the pixels by vias 431. Space among the vias 431 may be filled with a filler material 430, which may increase the mechanical stability of the connection of the electronics layer 420 to the radiation absorption layer 410. Other bonding techniques are possible to connect the electronic system 421 to the pixels without using vias.

Figure 4B:
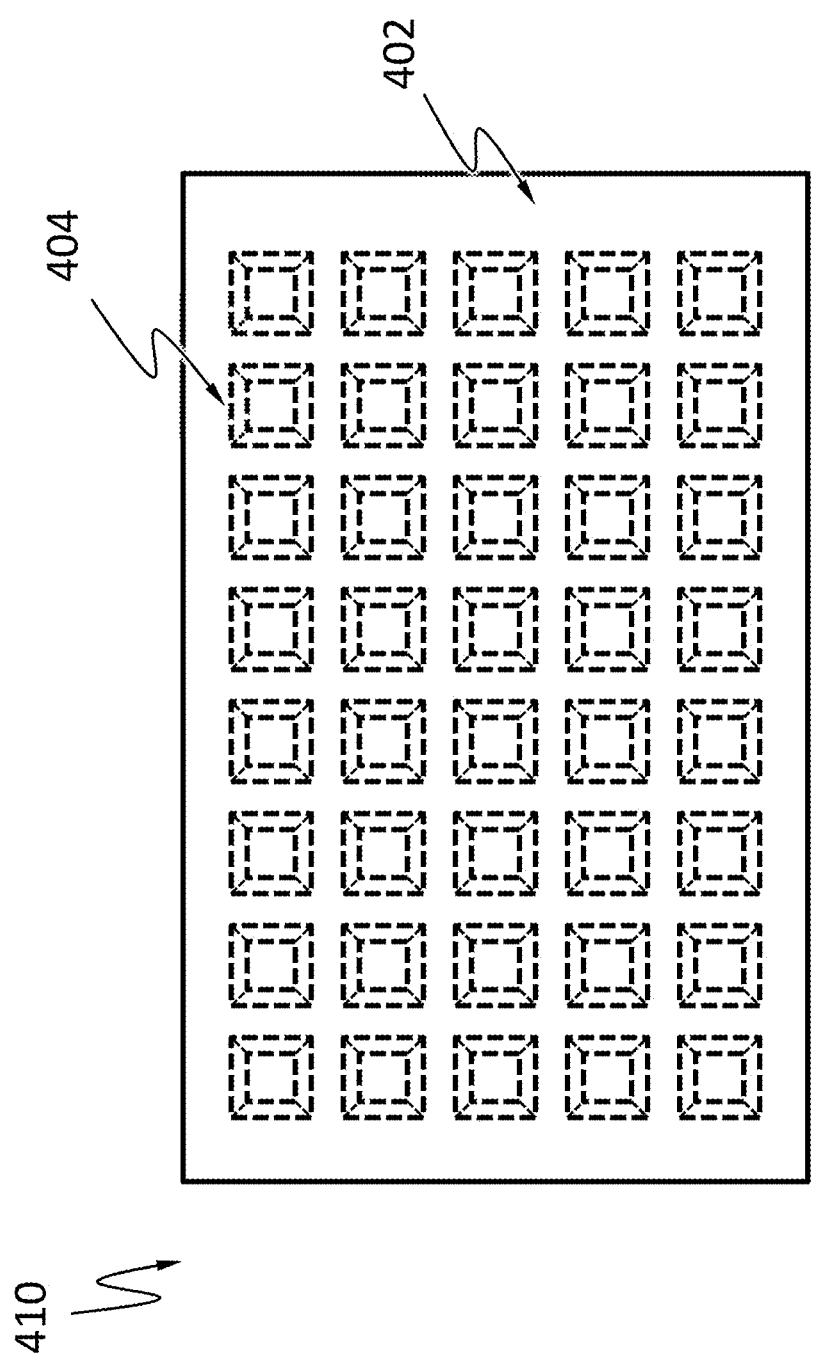
FIG. 4B schematically shows a top view of the radiation absorption layer in FIG. 4A, according to an embodiment.

FIG. 4B schematically shows a top view of the radiation absorption layer 410 in FIG. 4A, according to an embodiment. Each of the recesses 404 may have a shape of a frustum, prism, pyramid, cuboid, cubic or cylinder. The recesses 404 may be arranged into an array such as a rectangular array, a honeycomb array, a hexagonal array or any other suitable array. In example of FIG. 4B, the recesses 404 are arranged into a rectangular array, and each of the recesses 404 has a pyramid shape. The recesses 404 are shown in dashed line since they cannot be seen directly from the top view.

Figure 5:
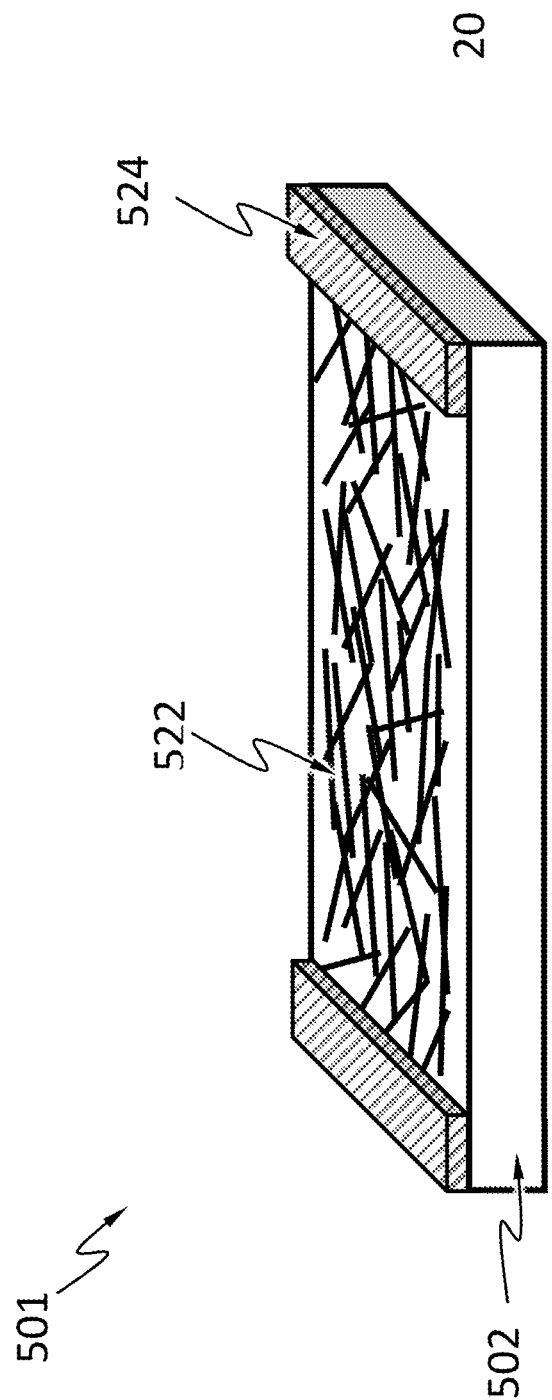
FIG. 5 schematically illustrates a process of forming an electrode, according to an embodiment.
Figure 5:
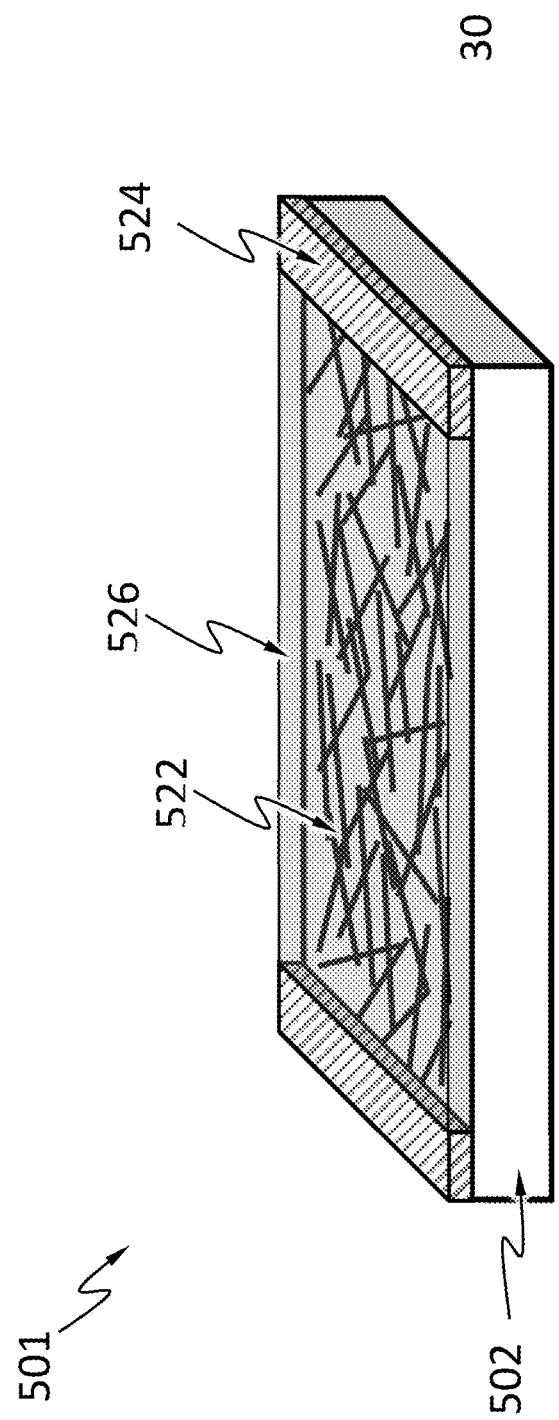

FIG. 5 schematically illustrates a process of forming an electrode 501, according to an embodiment. The electrode 501 may function as the electrode 301 in FIG. 3B, 3C or 419A in FIG. 4A.

In step 10, silver nanoparticles 522 is deposited onto a substrate 502. The substrate 502 may serve as the absorption region 310 or the heavily doped layer 302 in FIG. 3A or the semiconductor single crystals 406 in FIG. 4A. The silver nanoparticles 522 may serve as the silver nanoparticles 322 in FIG. 3A or 422 in FIG. 4A. The silver nanoparticles 522 may be deposited onto the substrate 502 by various techniques, including pressure dispensing, jet dispensing, spin coating, roll-to-roll coating, screen printing, inject printing, off-set printing and micro-contact printing, etc. For instance, silver nanoparticles 522 may be first uniformed dispersed in a polar or non-polar solvent (such as tetradecane, alcohol or water) with a suitable solid content (e.g., weight percentage around 30%-90%) to form a silver nanoparticle ink. The silver nanoparticle ink may be applied onto the substrate 502 by pressure dispensing with a dispensing system. A sintering or curing step may be followed to sinter the junctions (i.e., contact areas) among the silver nanoparticles 522 to reduce the resistance of the electrode 501 and to help removing the dispersing solvent. Sintering or curing may be done by annealing the electrode 501 under a suitable temperature (e.g., a temperature ranging from 100° C. to 700° C.) for a certain time duration (e.g., 10 minutes, 60 minutes, etc.). For instance, the electrode 501 may be cured below 200° C. when the substrate 502 is the semiconductor single crystals 406 such as cadmium zinc telluride (CdZnTe) single crystal or cadmium telluride (CdTe) single crystal. Other sintering or curing methods may also be used, such as laser annealing, mechanical pressing, plasmon-welding and local chemical wielding, etc.

In step 20, a conductive pad 524 is formed on the substrate 502, the conductive pad 524 being in electrical contact with a portion of the silver nanoparticles 522. The conductive pad 524 may be formed by depositing a conductive material (e.g., a metal such as Pt, Au or In, or any other suitable conducting materials) onto the substrate 502 by a suitable technique such as physical vapor deposition, chemical vapor deposition, spin coating, sputtering, etc. In the example of the step 20 of FIG. 5, the conductive pad 524 may comprise one or more regions on the edge of the substrate 502.

In an optional step 30, a coating layer 526 is coated onto the silver nanoparticles 522. The coating layer 526 may comprise insulating materials such as heat resistant polymers, or conductive materials such as conducting polymers, Indium tin oxide (ITO), graphene, silver, etc. Various coating methods may be applied depending on the choice of coating material. For instance, the coating layer 526 may comprise heat resistant polymers or conducting polymers, and may be formed by first coating or dispensing a polymer or monomer solution on to the silver nanoparticles 522, and then curing the polymer or monomer solution.

Figure 6:
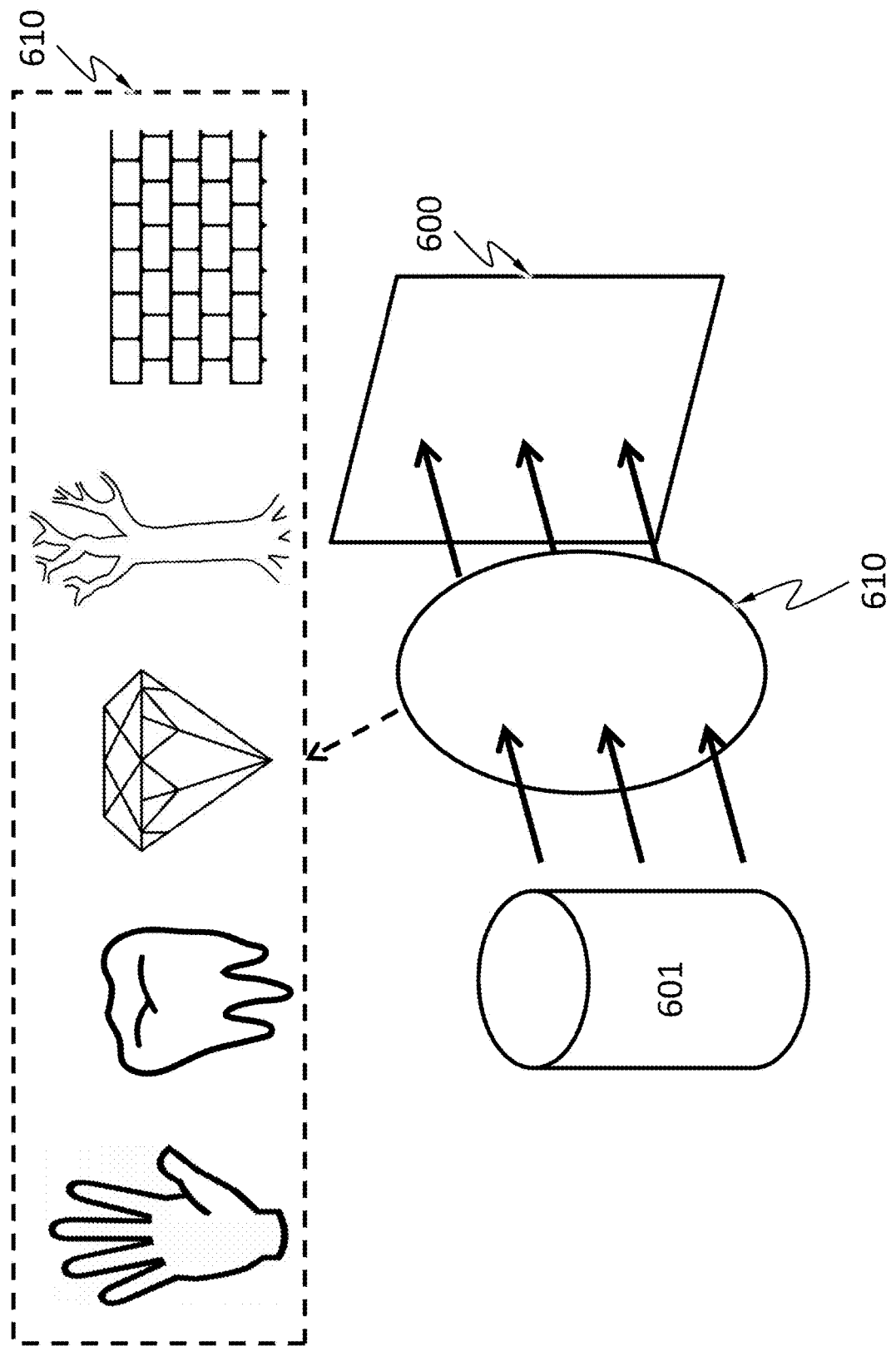
FIG. 6 schematically shows a system comprising the image sensor described herein.

FIG. 6 schematically shows a system comprising an apparatus 600 being the image sensor 300 or 400 described herein. The system comprises an X-ray source 601. X-ray emitted from the X-ray source 601 penetrates an object 610 (e.g., diamonds, tissue samples, a human body part such as breast), is attenuated by different degrees by the internal structures of the object 610, and is projected to the apparatus 600. The apparatus 600 forms an image by detecting the intensity distribution of the X-ray. The system may be used for medical imaging such as chest X-ray radiography, abdominal X-ray radiography, dental X-ray radiography, mammography, etc. The system may be used for industrial CT, such as diamond defect detection, scanning a tree to visualize year periodicity and cell structure, scanning building material like concrete after loading, etc.

Figure 7:
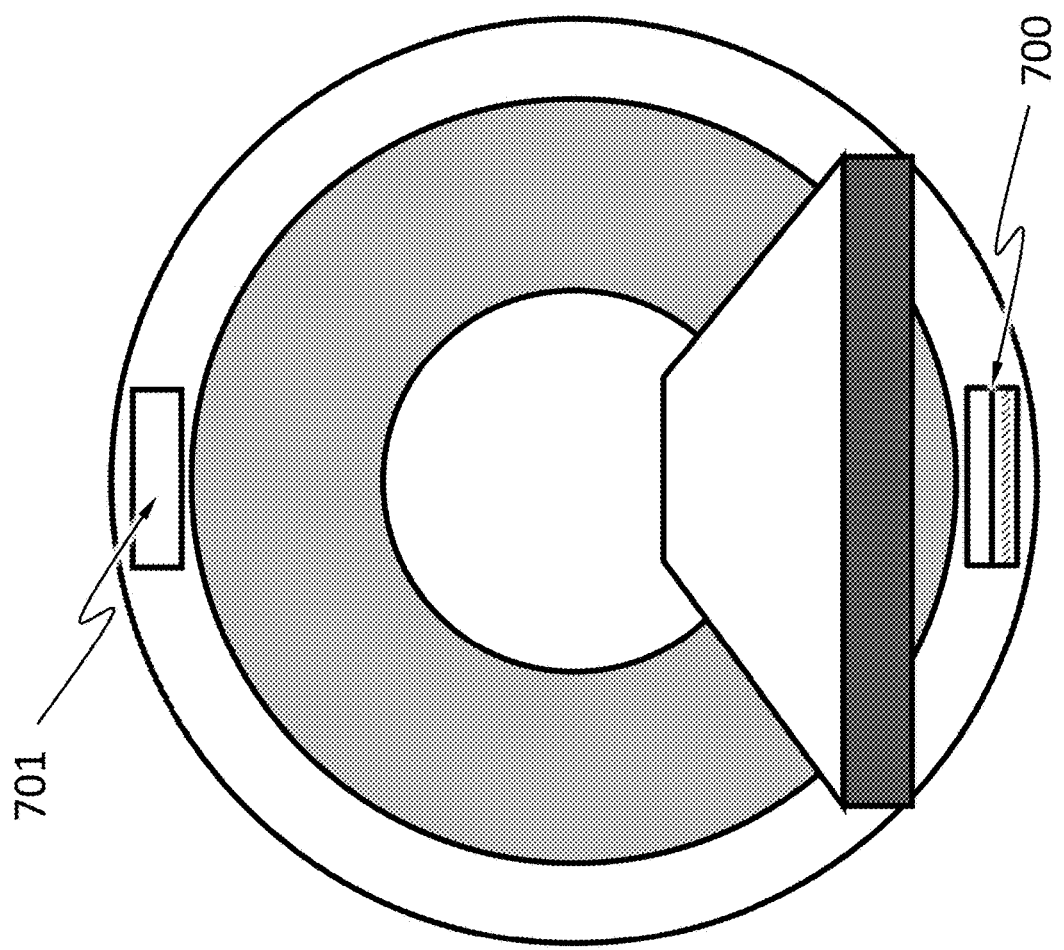
FIG. 7 schematically shows an X-ray computed tomography (X-ray CT) system.

FIG. 7 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises an apparatus 700 being the image sensor 300 or 400 described herein and an X-ray source 701. The apparatus 700 and the X-ray source 701 may be configured to rotate synchronously along one or more circular or spiral paths.

Figure 8:
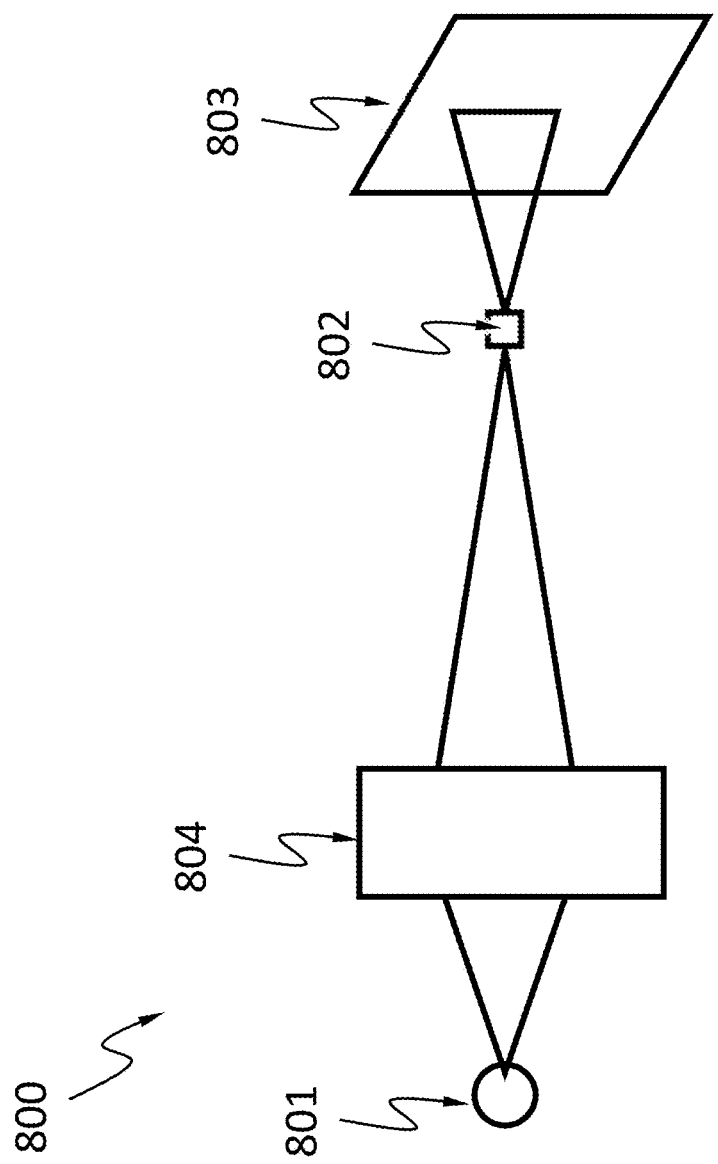
FIG. 8 schematically shows an X-ray microscope.

FIG. 8 schematically shows an X-ray microscope or X-ray micro CT 800. The X-ray microscope or X-ray micro CT 800 may include an X-ray source 801, focusing optics 804, and an apparatus 803 being the image sensor 300 or 400 described herein, for detecting an X-ray image of a sample 802.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
   an array of avalanche photodiodes (APDs), each of the APDs comprising an absorption region, an electrode and a first amplification region;
   wherein the absorption region is configured to generate charge carriers from a photon absorbed by the absorption region;
   wherein the electrode comprises silver nanoparticles and is electrically connected to the absorption region;
   wherein the first amplification region comprises a junction with an electric field in the junction;
   wherein the electric field is at a value sufficient to cause an avalanche of charge carriers entering the first amplification region, but not sufficient to make the avalanche self-sustaining;
   wherein the junctions of the APDs are discrete;
   wherein the silver nanoparticles comprise silver nanowires.

2. The apparatus of claim 1, wherein each of the APDs further comprises a second amplification region between the absorption region and the electrode, wherein the first amplification region and the second amplification region are on opposite sides of the absorption region.

3. The apparatus of claim 1, wherein a number density of the silver nanoparticles is above an electrical percolation threshold of the silver nanoparticles.

4. The apparatus of claim 1, wherein the electrode further comprises a conductive pad in electrical contact with a portion of the silver nanoparticles.

5. The apparatus of claim 1, wherein the electrode is a common electrode shared by the absorption regions of the array of APDs.

6. The apparatus of claim 1, wherein the electrode further comprises a coating layer on the silver nanoparticles.

7. The apparatus of claim 1, wherein the photon is a soft X-ray photon.

8. The apparatus of claim 1, wherein the absorption region has a thickness of 10 microns or above.

9. The apparatus of claim 1, wherein the absorption region comprises silicon.

10. The apparatus of claim 1, wherein an electric field in the absorption region is not high enough to cause avalanche effect in the absorption region.

11. The apparatus of claim 1, wherein the absorption region is an intrinsic semiconductor or a semiconductor with a doping level less than $10^{12}$ dopants/cm$^3$.

12. The apparatus of claim 1, wherein the absorption regions of at least some of the APDs are joined together.

13. The apparatus of claim 1, wherein the first amplification regions of the APDs are discrete.

14. The apparatus of claim 1, wherein the junction is a p-n junction or a heterojunction.

15. The apparatus of claim 1, wherein the junction comprises a first layer and a second layer, wherein the first layer is a doped semiconductor and the second layer is a heavily doped semiconductor.

16. The apparatus of claim 15, wherein the first layer has a doping level of $10^{13}$ to $10^{17}$ dopants/cm$^3$.

17. The apparatus of claim 15, wherein the first layers of least some of the APDs are joined together.

18. The apparatus of claim 15, wherein the junction is separated from a junction of a neighboring APD by a material of the absorption region, a material of the first or second layer, an insulator material, or a guard ring of a doped semiconductor.

19. The apparatus of claim 15, wherein the junction is separated from a junction of a neighboring APD by a guard ring of a doped semiconductor; wherein the doped semiconductor has a same doping type as the second layer and the guard ring is not heavily doped.

20. The apparatus of claim 15, wherein the junction further comprises a third layer sandwiched between the first and second layers; wherein the third layer comprises an intrinsic semiconductor.

21. The apparatus of claim 20, wherein the third layers of at least some of the APDs are joined together.

22. A system comprising the apparatus of claim 1 and an X-ray source, wherein the system is configured such that the apparatus forms an image of an object using X-ray from the X-ray source that penetrated the object.

23. An apparatus comprising:
a substrate;
a semiconductor single crystal in a recess in the substrate;
an electrode on the semiconductor single crystal;
wherein the semiconductor single crystal is configured to absorb radiation particles incident thereon and to generate charge carriers;
wherein the electrode comprises silver nanoparticles and is electrically connected to the semiconductor single crystal.

24. The apparatus of claim 23, wherein the silver nanoparticles are silver nanowires.

25. The apparatus of claim 23, wherein a number density of the silver nanoparticles is above an electrical percolation threshold of the silver nanoparticles.

26. The apparatus of claim 23, wherein the electrode further comprises a conductive pad in electrical contact with a portion of the silver nanoparticles.

27. The apparatus of claim 23, wherein the electrode further comprises a coating layer on the silver nanoparticles.

28. The apparatus of claim 23, wherein the semiconductor single crystal is a CdZnTe single crystal or a CdTe single crystal.

29. The apparatus of claim 23, wherein the substrate comprises silicon, germanium, GaAs or a combination thereof.

30. The apparatus of claim 23, wherein a surface of the semiconductor single crystal and a surface of the substrate are coextensive.

31. The apparatus of claim 23, further comprising
another electrode in electrical contact with the semiconductor single crystal;
an electronics layer bonded to the substrate, the electronics layer comprising an electronic system configured to process an electrical signal generated from the charge carriers collected by the other electrode.

32. The apparatus of claim 31, wherein the electronic system comprises a voltage comparator configured to compare a voltage of the electrode to a first threshold; a counter configured to register a number of radiation particles absorbed by the substrate; a controller; a voltmeter;
wherein the controller is configured to start a time delay from a time at which the voltage comparator determines that an absolute value of the voltage equals or exceeds an absolute value of the first threshold;
wherein the controller is configured to cause the voltmeter to measure the voltage upon expiration of the time delay;
wherein the controller is configured to determine a number of radiation particles by dividing the voltage measured by the voltmeter by a voltage that a single radiation particle would have caused on the other electrode;
wherein the controller is configured to cause the number registered by the counter to increase by the number of radiation particles.

33. A system comprising the apparatus of claim 23 and an X-ray source, wherein the system is configured such that the apparatus forms an image of an object using X-ray from the X-ray source that penetrated the object.

* * * * *